United States Patent [19]
Nash et al.

[11] Patent Number: 5,611,773
[45] Date of Patent: Mar. 18, 1997

[54] RANGE OF MOTION CAP FOR RANGE OF MOTION ORTHOTIC

[75] Inventors: Michael Nash, Danville; Gary Stafford, Hayward, both of Calif.

[73] Assignee: Orthopedic Technology Incorporated, Tracy, Calif.

[21] Appl. No.: 336,861

[22] Filed: Nov. 9, 1994

[51] Int. Cl.$^6$ .................................................. A61F 5/00
[52] U.S. Cl. ............................................. 602/16; 602/27
[58] Field of Search ................................. 602/16, 20, 23, 602/26, 27

[56] References Cited

U.S. PATENT DOCUMENTS

| | | | |
|---|---|---|---|
| 5,052,379 | 10/1991 | Airy et al. | 602/16 |
| 5,292,303 | 3/1994 | Bastyr et al. | 602/16 |
| 5,409,449 | 4/1995 | Nebolon | 602/16 |

Primary Examiner—Linda C. Dvorak
Attorney, Agent, or Firm—Townsend and Townsend and Crew

[57] ABSTRACT

An ankle pivot cap for the capture of a dorsiflexion detent pin and a plantar flexion detent pin is disclosed. Each respective pin is captured at its head with the flat pin head exposed to a resilient washer and the pin shank protruding from a restrictive track. Each path has shank capturing turns arrayed in a continuous "W" shaped path. Each of the shank capturing turns corresponds to a dorsiflexion limiting aperture or a plantar flexion limiting aperture. This correspondence allows shank protrusion with the respective dorsiflexion detent pin and plantar flexion detent pin held in spaced relation to the ankle pivot cap in precise relationship for insertion to corresponding dorsiflexion limiting apertures or plantar flexion limiting apertures on the orthotic. Consequently, adjustment of the orthotic is limited to cap removal, pin setting by movement to a pin capturing turn, followed by reinsertion of the cap to the ankle pivot. An adjustment protocol results allowing either patient or provider to rapidly set and easily adjust the disclosed range of motion appliance.

8 Claims, 2 Drawing Sheets

5,611,773

RANGE OF MOTION CAP FOR RANGE OF MOTION ORTHOTIC

This application relates to a range of motion orthotic. Specifically, a cap for retaining range of motion pins in position for removable attachment to and from a range of motion orthotic at the orthotic hinge is disclosed. In the removed position, the cap permits pin adjustment to changed range of motion intervals.

BACKGROUND OF THE INVENTION

Range of motion orthotics are known. Specifically, such orthotics are typically attached to the knee, ankle or elbow. They include a first limb capturing portion, a second limb capturing portion, and a pivotal joint therebetween. In the range of motion device, it is the purpose of the pivotal joint to restrict full limb motion to part limb motion to allow for recovery, usually from an injury, sprain, or surgery.

Prior art range of motion devices can be understood by the exemplary range of motion device utilized with this invention. Referring to FIG. 1, foot capturing portion F and calf capturing portion C are both shown connected by ankle pivot P.

A series of dorsiflexion setting holes 14 and plantar flexion holes 38 are provided. These respective holes move relative to ankle pivot P during relative motion between foot capturing portion F and calf capturing portion C.

Foot capturing portion F has underlying plate 28. Underlying plate 28 has dorsiflexion surface 29 and plantar flexion surface 30.

Operation of the prior art device is easy to understand. Dorsiflexion detent pin 32 is installed in a representative dorsiflexion limiting aperture 34. Likewise, plantar flexion detent pin 36 is installed in a representative plantar flexion limiting aperture 38. Dependent upon the respective ranges of motion sought, the particular apertures in dorsiflexion limiting aperture 34 and plantar flexion limiting aperture 38 will be chosen. For example, in the example here 20° dorsiflexion and 20° plantar flexion have been chosen.

Operation of the illustrated prior art is not without complication and inconvenience. Typically, the orthotic is adjusted that range of motion anticipated for both comfort and therapy before installation to the foot of the patient. This anticipated range of motion is usually not optimum and adjustment is required.

It is known to remove such appliances entirely, place the respective dorsiflexion detent pin 32 and plantar flexion detent pin 36 in new respective dorsiflexion limiting aperture 34 and plantar flexion limiting aperture 38 and repeat trial wearing of the orthotic. Alternately, personnel installing the device to the patient pull the orthotic pin—either by getting down on the floor or elevating the foot to which the orthotic is installed—and adjust the respective pins 32, 36.

The present invention is directed at simplifying this procedure.

SUMMARY OF THE INVENTION

A ankle pivot cap for the capture of a dorsiflexion detent pin and a plantar flexion detent pin is disclosed. Each respective pin is captured at its head with the flat pin head exposed to a resilient washer and the pin shank protruding from a restrictive track. Each path has shank capturing turns arrayed in a continuous "W" shaped path. Each of the shank capturing turns corresponds to a dorsiflexion limiting aperture or a plantar flexion limiting aperture. This correspondence allows shank protrusion with the respective dorsiflexion detent pin and plantar flexion detent pin held in spaced relation to the ankle pivot cap in precise relationship for insertion to corresponding dorsiflexion limiting apertures or plantar flexion limiting apertures on the orthotic. Consequently, adjustment of the orthotic is limited to cap removal, pin setting by movement to a pin capturing turn, followed by reinsertion of the cap to the ankle pivot. An adjustment protocol results allowing either patient or provider to rapidly set and easily adjust the disclosed range of motion appliance.

DESCRIPTION OF THE PREFERRED EMBODIMENT

Figure 1:
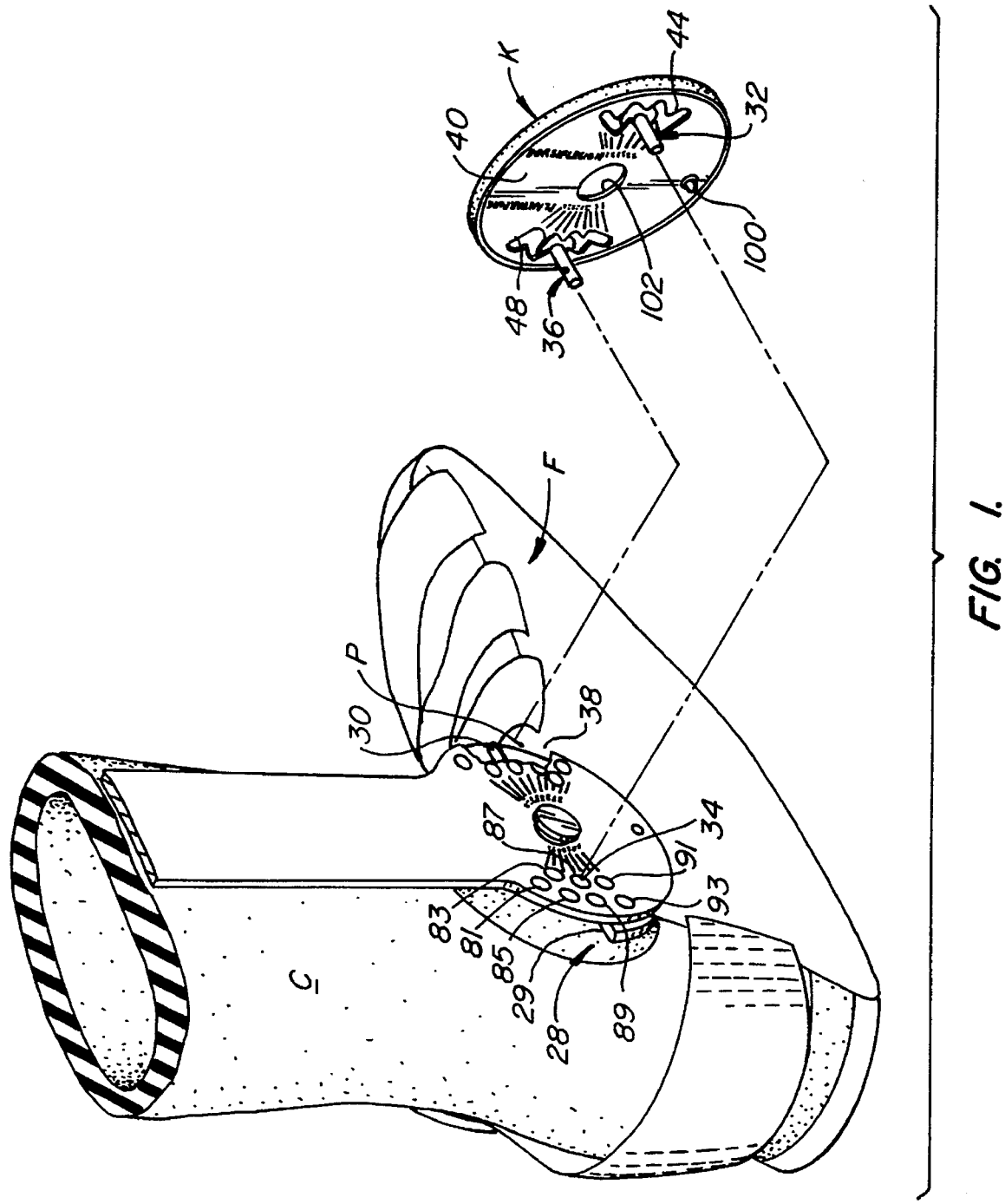
FIG. 1 is a perspective view of a prior art foot and ankle orthotic with the motion setting cap of this invention about to be installed with an exemplary range of motion setting.
Figures 2, 4:
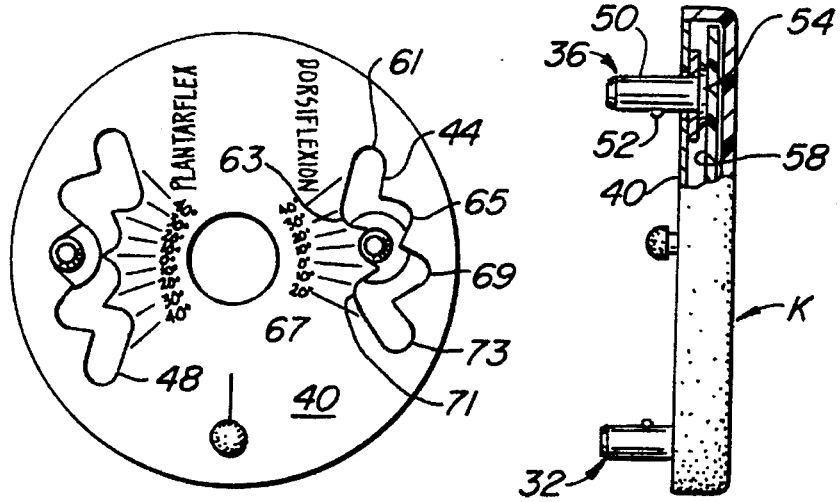
FIG. 2 is a cross-section of the pin retaining cap shown in FIG. 1 illustrating the detent pin retention of the pin head in the "W" shaped groove of the track with the protruding detent shank.
Figure 3:
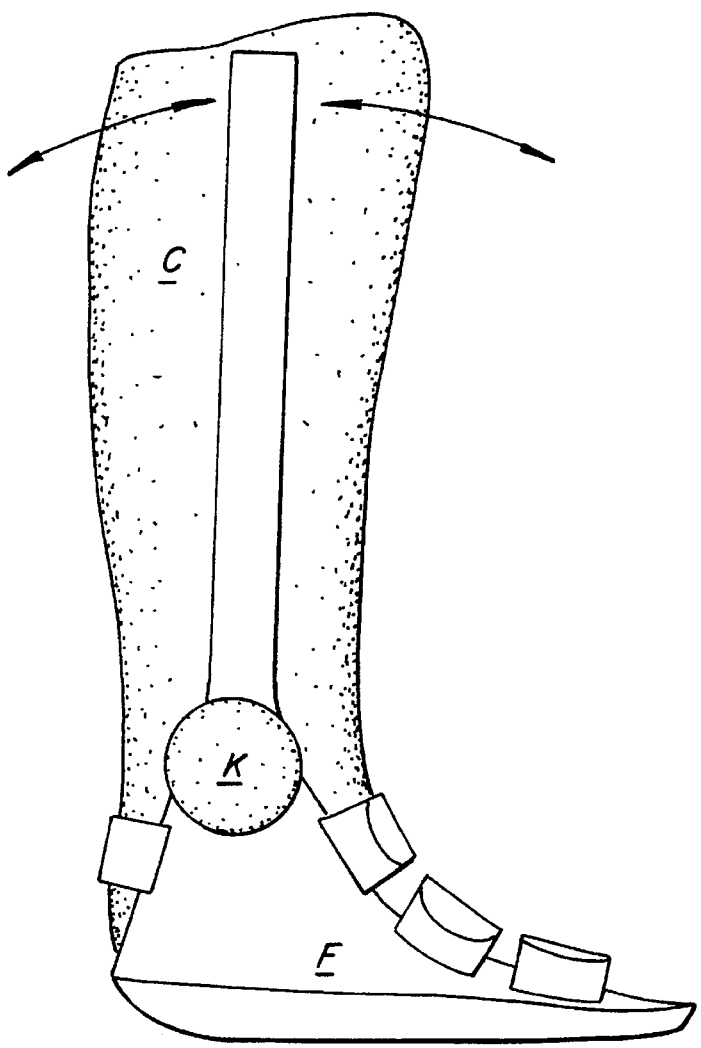
FIG. 3 is a view of the orthotic of FIG. 1 with the cap of this invention in place to define the readily set range of motion here required; and, FIG. 4 is a rear elevation of the cap of this invention illustrating the indicia utilized in locating the respective pins for limiting the range of motion.

Referring to FIG. 2, cap K is illustrated in side elevation section. Dorsiflexion detent pin 32 and plantar flexion detent pin 36 are illustrated captured to cap K by plate 40. Referring simultaneously to FIG. 2 and FIG. 4, the manner of such capture can be fully understood.

Plate 40 includes first dorsiflexion "W" shaped groove 44 and second plantar flexion "W" shaped groove 48. Each of the respective "W" shaped grooves has sufficient width to permit shank 50 to protrude outward of the "W" shaped groove. At the same time, head 54 of the respective pins 32, 36 is of sufficient dimension that respective grooves 44, 48 will not permit escape of the pins. For a backing providing a relatively high degree of lubricity to the pin capture, plastic backing 58 is placed inside cap K to facilitate movement of the respective pins 32, 36 to the respective desired positions.

Further examination of both first dorsiflexion "W" shaped groove 44 and second plantar flexion "W" shaped groove 48 will illustrate that the "W" shaped grooves assist in pin location. Specifically, and taking the case of first dorsiflexion "W" shaped groove 44, it will be observed that first extreme pin limit 61 and second extreme pin limit 73 correspond to +40° dorsiflexion movement limiting aperture 81 and −20° dorsiflexion movement limiting aperture 93. Likewise, it will be understood that each apex of "W" shaped groove 63, 65, 67, 69, 71 corresponds to the respective movement limiting apertures 83, 85, 87, 89, 91 for 30°, 20°, 10°, 0°, and −10° dorsiflexion Further, it will be understood that the inside of cap K is appropriately labeled. Having understood this much—and understanding that second plantar flexion "W" shaped groove 48 operates in a precisely analogous manner, operation of the device is easily summarized.

Initially, the brace will be set at an anticipated desired range of motion. Thereafter, adjustment will be effected by removing cap K and moving respective dorsiflexion detent pin 32 and plantar flexion detent pin 36 to new locations. Upon insertion of cap K to ankle pivot P with registration of respective detent pins 32, 36, immediate adjustment occurs.

To assure that registration is exact, it is preferred, but not required that cap K have lower protrusion 100 for fitting to 90° lock aperture of the illustrated range of motion orthotic. Likewise, aperture 102 fits about ankle pivot P centrally of cap K.

It will be understood that this invention can fit a wide variety of orthotic devices. These can include knee braces, elbow braces and the like. It is to be understood that the detachably adjustable range of motion cap here illustrated can be utilized widely in such braces.

What is claimed is:

1. In a range of motion device for an orthotic extending across a joint of the body between two connected relatively moving body portions, the range of motion device including;
    a hinge having first and second relatively moving hinge members;
    at least one of the relatively moving hinge members including a pivot and a series of apertures at defined locations off axis from the pivot for receiving a range of motion pin;
    the other of the relatively moving hinge members defining a surface for bearing against the range of motion pin for restricting movement of the hinge to a selected range of motion;
    a first sleeve section for capturing the first body portion, the first sleeve section having connection to the first relatively moving hinge member;
    a second sleeve section for capturing the second body portion, the second sleeve section having connection to the second relatively moving hinge member;
    the improvement comprising:
        a removably detachable cap for fitting over the hinge at the pivot and the series of apertures off axis from the pivot;
        a pin for restricting the range of motion of the hinge, the pin having a head portion and a shank portion, the shank portion of the pin being of sufficient length to enable the shank portion to penetrate a selected aperture for restricting the range of motion of the hinge;
        means for holding the pin for removal with the removably detachable cap, said means for holding including:
            a plate juxtaposed to the cap defining a groove;
            the plate with the groove permitting the juxtaposition of the plate to the cap permitting capture of the head portion of the pin with protrusion of the shank portion of the pin from the groove; and,
            defined locations on the groove for permitting registration of a pin to corresponding defined locations off axis from the pivot for holding the pin shank in position for penetration to one of the series of apertures to limit the range of motion of the hinge.

2. In a range of motion device for an orthotic extending across a joint of the body between two connected relatively moving body portions according to claim 1 and wherein:
    the groove is a W-shaped groove.

3. In a range of motion device for an orthotic extending across a joint of the body between two connected relatively moving body portions according to claim 2 and wherein:
    the groove has turning portions overlying at least one aperture of the series of apertures.

4. In a range of motion device for an orthotic extending across a joint of the body between two connected relatively moving body portions according to claim 3 and wherein:
    the turning portions of the groove are labeled with range of motion indicia.

5. In a range of motion device for an orthotic extending across a joint of the body between two connected relatively moving body portions, the range of motion device comprising:
    a hinge having first and second relatively moving hinge members;
    at least one of the relatively moving hinge members including a pivot and a series of apertures at defined locations off axis from the pivot for receiving a range of motion pin;
    the other of the relatively moving hinge members defining a surface for bearing against the range of motion pin for restricting movement of the hinge to a selected range of motion;
    a first sleeve section for capturing the first body portion, the first sleeve section having connection to the first relatively moving hinge member;
    a second sleeve section for capturing the second body portion, the second sleeve section having connection to the second relatively moving hinge member;
    a removably detachable cap for fitting over the hinge at the pivot and the series of apertures off axis from the pivot;
    a pin for restricting the range of motion of the hinge, the pin having a head portion and a shank portion, the shank portion of the pin being of sufficient length to enable the shank portion to penetrate a selected aperture for restricting the range of motion of the hinge;
    means for holding the pin for removal with the removably detachable cap, said means for holding including:
        a plate juxtaposed to the cap defining a groove;
        the plate with the groove permitting the juxtaposition of the plate to the cap permitting capture of the head portion of the pin with protrusion of the shank portion of the pin from the groove; and,
        defined locations on the groove for permitting registration of a pin to corresponding defined locations off axis from the pivot for holding the pin shank in position for penetration to one of the series of apertures to limit the range of motion of the hinge.

6. In a range of motion device for an orthotic extending across a joint of the body between two connected relatively moving body portions according to claim 5 and wherein:
    the groove is a W-shaped groove.

7. In a range of motion device for an orthotic extending across a joint of the body between two connected relatively moving body portions according to claim 6 and wherein:
    the groove has turning portions overlying at least one aperture of the series of apertures.

8. In a range of motion device for an orthotic extending across a joint of the body between two connected relatively moving body portions according to claim 7 and wherein:
    the turning portions of the groove are labeled with range of motion indicia.

* * * * *